United States Patent [19]

Bremus et al.

[11] Patent Number: 5,008,046

[45] Date of Patent: Apr. 16, 1991

[54] PROCESS FOR THE CONTINUOUS ESTERIFICATION OF FATTY ACIDS

[75] Inventors: Norbert Bremus, Langenfeld; Bernhard Gutsche, Hilden; Lutz Jeromin, Hilden; Eberhard Peukert, Hilden; Bernard Schleper, Duesseldorf, all of Fed. Rep. of Germany

[73] Assignee: Henkel Kommanditgesellschaft auf Aktien, Duesseldorf, Fed. Rep. of Germany

[21] Appl. No.: 326,592

[22] Filed: Mar. 21, 1989

[30] Foreign Application Priority Data

Mar. 21, 1988 [DE] Fed. Rep. of Germany ....... 3809417

[51] Int. Cl.$^5$ .......................... C11C 3/00; C07C 67/08
[52] U.S. Cl. .......................... 260/410.6; 260/410.9 R; 560/263; 560/265
[58] Field of Search ..................... 260/410.6, 410.9 R; 560/231, 263, 265

[56] References Cited

U.S. PATENT DOCUMENTS 4,381,407  4/1983  Bremus et al. .................... 560/263

FOREIGN PATENT DOCUMENTS 0082301  6/1983  European Pat. Off. .
2503195  7/1976  Fed. Rep. of Germany .

OTHER PUBLICATIONS

H Stage Chemiker—Ztg./Chem. Apparatur 87, No. 18, pp. 661–666 (1963).

*Primary Examiner*—Jose G. Dees
*Assistant Examiner*—Vera C. Clarke
*Attorney, Agent, or Firm*—Ernest G. Szoke; Wayne C. Jaeschke; Daniel S. Ortiz

[57] ABSTRACT

The invention is a process for the continuous liquid-phase esterification of $C_2$-$C_{24}$ fatty acids with alkanols in countercurrent contact and reaction in a reaction column, the catalysts and fatty acids are introduced at the top plate and the alkanols below the lowest plate, at a head pressure of the reaction column of 200 to 900 hPa. The process reduces dehydration of the alkanols.

14 Claims, 1 Drawing Sheet

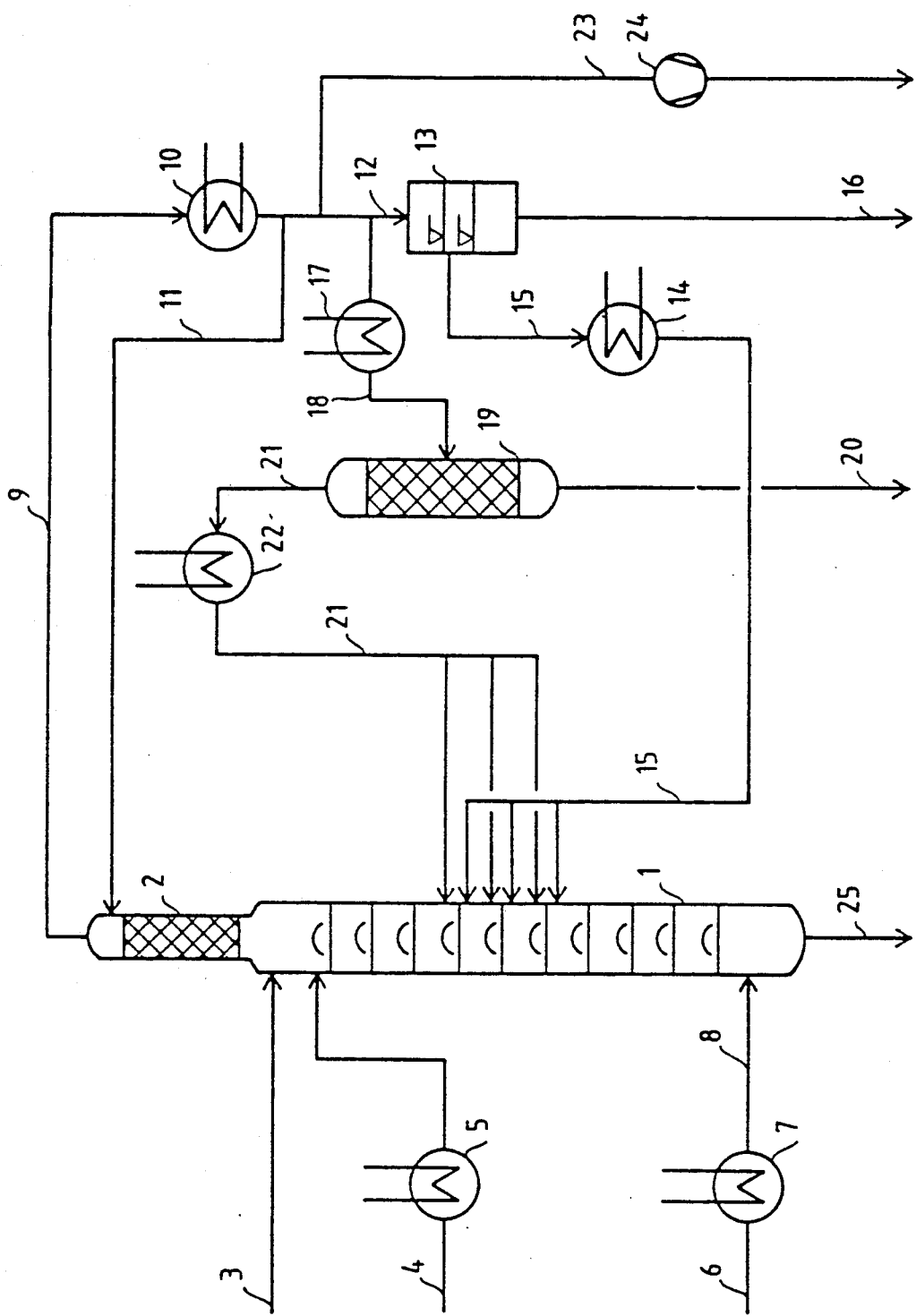

PROCESS FOR THE CONTINUOUS ESTERIFICATION OF FATTY ACIDS

BACKGROUND OF THE INVENTION

1. Field of the Invention

The invention is a process for the continuous esterification of $C_2$–$C_{24}$ fatty acids with $C_1$–$C_5$ monoalkanols or $C_2$–$C_3$ dialkanols in the liquid phase, at an elevated temperature, in the presence of catalysts. The catalysts and the heated fatty acid are fed to the uppermost plate and the alkanols are introduced in the vapor phase above the sump at the lowermost plate of a multiple-plate reaction column followed by a rectifying section. The fatty acids and alkanols are reacted countercurrently over a residence time of the alkanols in the liquid phase of the reaction column of at least 20 minutes. A water/alkanol mixture is removed through the rectifying section and the fatty acid ester is removed from the sump of the column.

2. Statement of Related Art

Processes of the type mentioned above for the continuous esterification of fatty acids are known, cf. H. Stage, Chemiker-Ztg./Chem. Apparatur 87. No. 18, 661–666 (1963). This publication describes the esterification of fatty acids with methanol and n-butanol in multiplate reaction columns with steam baffle plates operated at normal pressure. However, the continuous esterification of fatty acids, on an industrial scale, is carried out in several stages in plate columns operated at pressures of from 5 to 30 bar, cf. DE-C 25 03 195.

It has been discovered that, in conventional processes for the continuous esterification of fatty acids, dehydration occurs to an unacceptable extent, for example where branched monoalkanols, such as isopropanol, are used. Accordingly, it is an object of the present invention to provide a process in which the unwanted secondary reactions are suppressed or substantially reduced.

BRIEF SUMMARY OF THE INVENTION

Other than in the operating examples, or where otherwise indicated, all numbers expressing quantities of ingredients or reaction conditions used herein are to be understood as modified in all instances by the term "about".

According to the invention, the object is achieved by a process for esterification of $C_2$–$C_{24}$ fatty acids with $C_1$–$C_5$ monohydric alcohols or $C_2$–$C_3$ dihydric alcohols wherein the esterification is carried out at a head pressure of the reaction column in the range from 200 to 900 hPa and preferably in the range of 700 to 900 hPa. The formation of propene for example, which exceeds 5%, based on the isopropanol used, according to the prior art, can be reduced to less than 0.1%. In addition, the esterification according to the invention, in contrast to that according to DE-C- 25 03 195, can be carried out in a single reaction column, thereby reducing investment costs. Conversions of more than 99% can be achieved with the process according to the invention.

BRIEF SUMMARY OF THE DRAWING

The FIGURE is a diagrammatic representation of an embodiment of the process of the invention.

DETAILED DESCRIPTION OF THE INVENTION

The reaction column used for the process of the invention can be selected from standard plate columns, such as sieve-plate columns and, preferably bubble plate columns having high liquid levels and hold-up. Typical columns are described in EP-B-0 033 929 and in DE-A-31 46 142.

In one preferred embodiment, the process of the invention is used for the esterification of $C_6$–$C_{20}$ fatty acids or mixtures of such fatty acids of natural, for example vegetable, animal and/or sea-animal origin or of synthetic origin. These include the so-called "first-cut" fatty acids (6 to 12 C atoms) obtained in large quantities in the working up of fatty acid mixtures of natural origin.

In another preferred embodiment of the invention, the esterification is carried out with $C_2$–$C_5$ alkanols, more especially ethanol, propanol, butanol, and pentanol, and isomers thereof, although methanol may also be used. With ethylene glycol or propylene glycol it is possible to produce full esters and/or partial esters of these dialkanols.

In another preferred embodiment of the invention, the esterification is carried out at a temperature at the top of the reaction column of at most 190° C. and more preferably in the range from 120° C. to 145° C. These esterification temperatures which are low by comparison with conventional processes lead in particular to a reduction in the necessary energy costs of the process.

Another preferred embodiment of the process is characterized by the use of esterification catalysts from the group consisting of sulfuric acid, toluenesulfonic acid, chlorosulfonic acid and methylsulfonic acid. It is preferred to use p-toluenesulfonic acid which accumulates in the column bottoms (sump) during the process and may readily be removed therefrom.

In another preferred embodiment of the invention, monoalkanols and fatty acids are used in molar ratios of less than 2:1, preferably in molar ratios of from 1.1:1 to 1.8:1 and more preferably in molar ratios of from 1.2:1 to 1.4:1. A substantially quantitative conversion of the fatty acids is obtained even with these low molar ratios. Where dialkanols are used, the molar ratios of the fatty acids to dialkanols are adapted accordingly, in consideration of the desired end products (partial and/or full esters).

In another preferred embodiment of the invention, the fatty acids are heated before being introduced into the reaction column.

In another preferred embodiment of the invention, the water/alkanol mixture removed from the rectifying section of the reaction column is partially returned as a reflux stream to the rectifying section, optionally after separation of excess water, thus preventing the entrainment of fatty acid ester in the head product.

In another preferred embodiment of the invention, the water/alkanol mixture removed from the rectifying section, optionally after separation of excess water, is returned at least partly as an azeotrope to the reaction column at a point where the molar ratio of water to alkanol in the column has approximately the composition of the azeotrope. This eliminates the need for complex and expensive measures for removing the water present in the azeotropes.

A preferred process for carrying out the invention is described in detail in the following drawing, which is a flow chart of the process according to the invention for the continuous esterification of fatty acids. The key component of the process is a reaction column 1, comprising a plurality of bubble plates, surmounted by the rectifying section 2. The catalyst or catalyst solution, optionally after heating, is delivered through a pipe 3 to the uppermost plate of the reaction column 1, as is the fatty acid (through a pipe 4), the fatty acid being heated by means of a heat exchanger 5 before delivery to the reaction column. The fresh alkanol is delivered through a pipe 6 to a second heat exchanger 7, superheated and directly introduced into the reaction column 1 through a pipe 8 immediately above the sump of the column. Fresh alkanol refers to alkanol which has not been recycled through the process.

In operation of the column, the water/alkanol mixture formed is removed through pipe 9 at the head of the rectifying section 2 and condensed in the heat exchanger 10. Part of the stream is returned as reflux through pipe 11 to the head of the rectifying section 2 to prevent fatty acids from being entrained in pipe 9.

In the case of systems which are immiscible under the condenser conditions, the other part of the stream of the pipe 9 is delivered through pipe 12 to separator 13. After superheating in a heat exchanger 14, the lighter organic phase from the separator is fed through a pipe 15 to the reaction column 1 at the point at which the molar ratio of alkanol to water in the reaction column has substantially the composition of the stream in the pipe 15. The aqueous phase from the separator 13 is removed from the system through a pipe 16.

In the case of systems which are miscible, the residual stream is heated in a heat exchanger 17 and fed through a pipe 18 to a rectifying column 19. The aqueous sump product is removed from the system through a pipe 20. The head product, which accumulates in the form of an azeotrope except in the case of methanol, is delivered through a pipe 21 to a heat exchanger 22 in which it is superheated and then fed—similarly to the stream of the pipe 15—to the reaction column 1 at that point at which the molar ratio of water to alkanol in the reaction column has substantially the composition of the stream of the pipe 21.

The pressure in the reaction column 1 is regulated through a pipe 23 and a vacuum pump 24.

The sump product of the reaction column 1, which comprises fatty acid ester, optionally with catalyst, is removed through pipe 25.

In steady-state operation of the reaction column, the esterification reaction takes place on the plates countercurrently with superimposed absorption/desorption.

A column similar to that described in DE-A-31 46 142 was used for the following Examples. The column had a diameter of 36 cm and 30 plates with 10 bubble caps. The rectifying section surmounting the column comprised two wire mesh packs (each 1.1 m long) made by the Montz company.

EXAMPLE 1

Esterification of a $C_{14}$ Fatty Acid with Fresh Isopropanol

Process parameters:
Fatty acid feed: 110 kg/hr
Isopropanol feed: 51 kg/hr
Molar ratio of fatty acid to isopropanol: 1:1.8
Temperature of isopropanol: 140° C.
Temperature of the $C_{14}$ fatty acid 135° C.
Residence time of the fatty acid 3.3 hours
Column temperature 130° C. -140° C. Measured at the top bubble cap tray
Catalyst: p-toluenesulfonic acid, 1% by weight, based on $C_{14}$ fatty acid
Head pressure of the reaction column 800 hPa
Propene formation, based on isopropanol, less than 0.1%.

When the reaction was carried out in the same reaction column under a slight excess pressure and a correspondingly higher column temperature, the formation of propene, based on isopropanol, increased to more than 5%.

EXAMPLE 2

Esterification of a Technical $C_{14}$ Fatty Acid with Fresh Isopropanol and Isopropanol Azeotrope Process parameters:
Fatty acid feed: 110 kg/hr
Isopropanol feed: 28.8 kg/hr
Molar ratio of $C_{14}$ fatty acid to fresh isopropanol 1:1
Molar ratio of $C_{14}$ fatty acid to isopropanol (azeotrope) 1:0.5
Temperature of fresh isopropanol: 140° C.
Temperature of isopropanol azeotrope: 120° C.
Temperature of $C_{14}$ fatty acid 135° C.
Residence time of the $C_{14}$ fatty acid 3.3 hours
Column temperature 130° C.-140° C. Measured at the top bubble cap tray
Catalyst: p-toluenesulfonic acid, 1% by weight, based on fatty acid
Head pressure of the reaction column 800 hPa
Propene formation: less than 0.1%, based on isopropanol.

We claim:

1. A continuous process for esterification of $C_2$-$C_{24}$ fatty acid with $C_1$-$C_5$ monohydric alkanol or $C_2$-$C_3$ dihydric alkanol in a liquid phase in the presence of a catalyst which . comprises:
    (a) introducing heated fatty acid and catalyst onto the top plate of a multiple plate reaction column, operated at a top pressure of from about 200 to about 900 hPa, the top of the reaction column is in communication with a rectifying column;
    (b) introducing the alkanol, in a vapor phase, below the lowest plate of the reaction column;
    (c) reacting the fatty acid and the alkanol in the liquid phase;
    (d) removing a water-alkanol vapor mixture through the rectifying column; and
    (e) removing an esterified fatty acid mixture from the column below the lowest plate.

2. A process of claim 1 wherein the esterification is carried out at a pressure at the top of the reaction column in the range from about 700 to about 900 hPa.

3. A process of claim 1 wherein $C_6$-$C_{20}$ fatty acid is esterified.

4. A process of claim 1 wherein the fatty acid is esterified with $C_2$-$C_5$ alkanol.

5. A process of claim 1 wherein the esterification is carried out a temperature at the top plate of the reaction column not higher than about 190° C.

6. A process of claim 5 wherein the temperature at the top plate of the reaction column is in the range of from about 120° C. to about 145° C.

7. A process of claim 1 wherein the esterification catalyst comprises at least one member selected from the group consisting of sulfuric acid, toluenesulfonic acid, chlorosulfonic acid and methylsulfonic acid.

8. A process of claim 1 wherein the monohydric alkanol and fatty acid are introduced into the reaction column in a molar ratio of less than 2:1.

9. A process of claim 8 wherein the molar ratio is from about 1.1:1 to about 1.8:1.

10. A process of claim 9 wherein the monohydric alkanol and fatty acid are introduced in a molar ratio of from about 1.2:1 to about 1.4:1.

11. A process of claim 1 wherein a portion of the water/alkanol mixture removed from the rectifying section is returned to the rectifying section.

12. A process of claim 11 wherein water is separated from the alkanol/water mixture before the alkanol is returned to the rectifying section.

13. A process of claim 1 wherein a portion of the water/alkanol mixture removed from the rectifying section, after separation of excess water, is returned as an azeotrope to the reaction column at a point where the molar ratio of water to alkanol in the column has substantially the composition of the azeotrope.

14. A process of claim 1 wherein the residence time of the alkanol in the reaction column is at least about 20 minutes.

* * * * *

UNITED STATES PATENT AND TRADEMARK OFFICE
CERTIFICATE OF CORRECTION

PATENT NO. : 5,008,046

DATED : April 16, 1991

INVENTOR(S) : Bremus et al.

It is certified that error appears in the above-identified patent and that said Letters Patent is hereby corrected as shown below:

At Column 4, in claim 3, line 57, after "A process of Claim" insert --1--.

Signed and Sealed this

Fifteenth Day of September, 1992

Attest:

DOUGLAS B. COMER

*Attesting Officer*  *Acting Commissioner of Patents and Trademarks*